United States Patent
Yang

(10) Patent No.: US 6,410,050 B1
(45) Date of Patent: Jun. 25, 2002

(54) CELLULOSE CAPSULE USING MIXED SOLUTION OF PECTIN AND GLYCERIN AND THE MANUFACTURING PROCESS THEREOF

(75) Inventor: Joo Hwan Yang, Bucheon (KR)

(73) Assignee: Suheung Capsule Co., Ltd., Bucheon (KR)

(*) Notice: Subject to any disclaimer, the term of this patent is extended or adjusted under 35 U.S.C. 154(b) by 0 days.

(21) Appl. No.: 09/544,115

(22) Filed: Apr. 6, 2000

(30) Foreign Application Priority Data

Mar. 6, 2000 (KR) .......................... 2000-10990

(51) Int. Cl.[7] .................. A61K 9/48; A61K 9/64
(52) U.S. Cl. ............... 424/451; 424/400; 424/456; 514/962
(58) Field of Search ................ 424/400, 451, 424/456; 514/962

(56) References Cited

U.S. PATENT DOCUMENTS

| | | | | |
|---|---|---|---|---|
| 4,044,153 A | * | 8/1977 | Schultz et al. | 424/330 |
| 4,624,945 A | * | 11/1986 | Eckenhoff et al. | 514/30 |
| 4,627,850 A | * | 12/1986 | Deters et al. | 604/892 |
| 5,431,917 A | | 7/1995 | Yamamoto et al. | 424/451 |
| 5,574,150 A | * | 11/1996 | Yaginuma et al. | 536/56 |

FOREIGN PATENT DOCUMENTS

WO            WO98/27151            6/1998

* cited by examiner

Primary Examiner—Thurman K. Page
Assistant Examiner—Charesse Evans
(74) Attorney, Agent, or Firm—Jacobson Holman, PLLC

(57) ABSTRACT

The present invention provides a cellulose capsule comprising the steps of: i) preparing a mixed solution of pectin and glycerin, ii) adding said mixed solution to solubilized cellulose aqueous solution, iii) adding a small amount of glacial acetic acid, calcium gluconate, sucrose fatty acid ester to said mixture, and iv) standing by adjusting viscosity and forming a capsule.

12 Claims, 1 Drawing Sheet

CELLULOSE CAPSULE USING MIXED SOLUTION OF PECTIN AND GLYCERIN AND THE MANUFACTURING PROCESS THEREOF

BACKGROUND OF THE INVENTION

The present invention relates to a cellulose hard capsule prepared using the mixed solution of pectin and glycerin and its preparation method thereof.

Hard capsules are widely used in the pharmaceutical industry as well as in the health food supplement market. The main usage thereof is as dosage form for solid, semi-solid, liquid, pellet or herbal preparations. A primary objection of these dosage forms is to have a good disintegration after being administered in order to enable an effective dissolution of the active substances in the appropriate digestive organ. Consequently, this disintegration characteristic has to remain stable over time when finished products are stored prior to use.

The traditional material for forming the capsule is gelatin, because it has the correct and quite ideal properties. Nevertheless, gelatin has some disadvantages which make it necessary to have other capsule materials available. A major unfavorable aspect is the animal origin of gelatin. Other disadvantages are the inconveniences of relatively high water content (10~16%) and the loss of elasticity with decreasing water content. Furthermore gelatin capsules are sensitive to heat and humidity which affects the usability of the product.

As a gelatin substitute the use of water soluble capsule, the cellulose derivatives have been disclosed in some literatures. However, in the case of using cellulose derivatives as capsule material, the gelling agent has to be included in the capsule composition.

U.S. Pat. No. 5,431,917 disclosed a method for preparing cellulose hard capsule using the carrageenan as gelling agent and potassium ion as co-gelling agent. Further, WO 98/27151 disclosed a cellulose capsule using gellan gum as gelling agent. Even though pectin had been expected in this publication as a gelling agent equivalent to gellan gum or carrageenan, the pectin itself cannot be used as a gelling agent due to its low gelling property caused by the hydrolysis of pectin when it is applied to cellulose capsule.

Pectin is a hydrocolloidal compound used as thickening agent, jellifying agent or texturizer in food processing, especially, in jam, jelly or squeezed juice processing. If pectin is applied to hard capsule component, it makes hard capsule be stable compared to other gelling agent on condition that pectin overcomes the problem of hydrolysis property.

Pectin is a kind of polysaccharide forming a plant tissue as colloidal material, which consists of methylester of polygalacturonic acid bound to hemicellulose or α-cellulose.

Pectin can be classified into three groups under the degree of methyl esterification of carboxyl group in a pectin molecule; i) high methoxyl pectin: more than 50% of degree of esterification and more than 7% of methoxyl content; ii) low methoxyl pectin: less than 50% of degree of esterification and less than 7% of methoxyl content; iii) low methoxyl amide pectin: amine radical is replaced by methyl radical in esterification.

All of pectins can be reacted with calcium. Through the reaction with calcium, high methoxyl pectin slightly increases its viscosity, whereas low methoxyl pectin forms flexible gel. However, according to the lapse of time for reaction or storage, the gel formation property suddenly declines due to the hydrolysis of pectin molecule.

Although pectin has above drawbacks, it may be used successfully in confectionery industry for gum, cookie, jelly etc. However, due to the hydrolysis of pectin molecule in the mixed solution, it can not be used for gelling agent to the preparation process of cellulose capsule, which comprises following steps of: i) dispersing mixed solution over 80° C. and solubilizing it under 50° C. at least for 24~36 hours; ii) stabilizing the solution at 53~55° C. after adjusting the viscosity and removal of bubble; and iii) forming a capsule using molding pin. Therefore, the mixed solution for making hard capsule has to be continuously gelled more than 20 hours for making a film If pectin is used as gelling agent for making cellulose capsule, we can not obtain a desirable product, because gelling property of pectin declines only after 12 hours gellation caused by hydrolysis of pectin molecule.

To solve above drawback of pectin, the present invention developed a process for preparing cellulose capsule using pectin mixed solution, which does not decline the gelling property over a lapse of more than 12 hours.

SUMMARY OF THE INVENTION

The object of the present invention is to provide a process for preparing cellulose capsule comprising the steps of: i) preparing a mixed solution of pectin and glycerin, ii) adding said mixed solution to solubilized cellulose aqueous solution, iii) adding a small amount of glacial acetic acid, calcium gluconate, sucrose fatty acid ester to said mixture, and iv) standing by adjusting viscosity and forming a capsule.

Another object of the present invention is to provide a cellulose capsule comprising i) 15~23 wt % of cellulose derivatives, ii) 0.3~1.1 wt % of low methoxyl amide pectin, and iii) 0.04~0.6 wt % of glycerin.

The other object of the present invention is to provide a cellulose capsule comprising i) 18~20 wt % of cellulose derivatives, ii) 0.6~0.8 wt % of low methoxyl amide pectin, iii) 0.1~0.3 wt % of glycerin, iv) 0.03~0.05 wt % of glacial acetic acid, v) 0.03~0.05 wt % of calcium gluconate, and vi) 0.2~0.5 wt % of sucrose fatty acid ester.

DETAILED DESCRIPTION OF THE INVENTION

Figure 1:
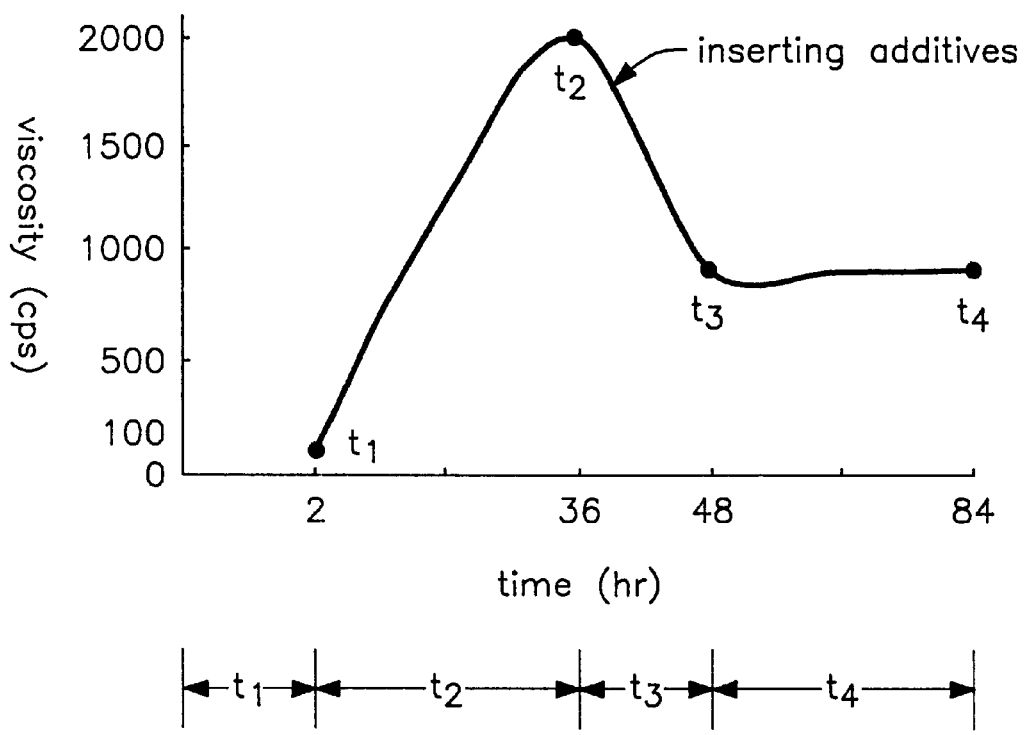
FIG. 1 shows the curve of the viscosity of the mixed aqueous solution according to the flow of time.

To prepare the cellulose capsule in continuous process, the gellation process has to be maintained at least 20 hours after solubilizing the mixture. For this purpose, the gellation of the mixed solution of pectin and glycerin has to be maintained more than 20 hours without hydrolysis of pectin.

Further, the order of adding the components also influences the gellation of mixture for making a cellulose capsule. Followings are steps and methods for preparing a cellulose capsule of the present invention.

In the first step, hydroxypropylmethylcellulose (HPMC) is added to the purified water at 80~85° C. without making an agglomerate. Then, the mixture is stirred and dispersed at 250~350 rpm for 90~150 minutes. After dispersion, the dispersed aqueous solution is stirred and solubilized until 45~50° C. Then, the mixture is cooled in room temperature by standing naturally for 24~36 hours. The solution becomes dark brown when finishing solubilization.

The mixed solution of pectin and glycerin is prepared by following steps of: i) pectin is added to the purified water at 60° C. by stirring at 8,000~10,000 rpm, ii) glycerin is added to said mixture after solubilization of pectin, and iii) stirring the mixture continuously to make a mixed solution.

The solution of calcium gluconate is prepared using about 60° C. purified water by stirring at 3,000 rpm for about 3 minutes.

Followings are preparation steps for making a cellulose capsule.

i) Stirring for 5 minutes after solubilizing HPMC
ii) Stirring for 5 minutes after adding the mixed solution of pectin and glycerin;
iii) Stirring for 2 minutes after adding the glacial acetic acid;
iv) Stirring for 2 minutes after adding the calcium gluconate;
v) Stirring for 10 minutes after adding sucrose fatty acid ester; and
vi) Standing the solution prepared in above step.

Such prepared solution is packed in the bottle, and is heated up to 53~55° C. by standing for 10~14 hours. Then, the viscosity is adjusted and the bubble is completely removed for forming a capsule. The desirable hard capsule having appropriate thickness and weight can be obtained after forming a capsule using molding pin.

Pectin is not hydrolyzed during more than 48 hours continuous manufacturing test. Therefore, there is no problem by losing the mixture from the molding pin. The quality of cellulose hard capsule prepared in this invention can be maintained during the long drying without any change of film.

The present invention will be more specifically explained by the following examples and comparative examples. However, it should be understood that the examples are intended to illustrate but not in any manner to limit the scope of the present invention.

Comparative Example 1

37 g of calcium gluconate (0.04% Conc.) is added to 70.1 L of purified water (80~85° C.) and dissolved for 5 minutes. Then, 18.5 kg of HPMC (19.34% Conc.) is added without making an agglomerate, and the mixture is stirred and dispersed at 300 rpm for 120 minutes. After dispersion, the dispersed aqueous solution is stirred, solubilized and cooled naturally until 45~50° C. for 24~36 hours. The solution becomes dark brown when finishing solubilization.

The pectin solution is prepared by adding 703 g of pectin (0.74% Conc.) to 6.3 L of purified water at 60° C. by stirring from 8,000 rpm to 9,700 rpm. The prepared pectin solution is added to solubilized HPMC mixed solution.

Then, such prepared solution is packed in the bottle, and is heated up to 53~55° C. by standing for 12 hours. Then, the viscosity is adjusted and the bubble is completely removed for forming a capsule.

However, we can not obtain the desirable hard capsule having appropriate thickness and weight can be obtained after forming a capsule using molding pin, because pectin is hydrolyzed during the process and gellation activity is declined.

Comparative Example 2

To overcome the problem of pectin hydrolysis, the plasticizers, such as, glycerin, glacial acetic acid and sucrose fatty acid ester are added to the mixed solution. The cellulose capsule is prepared as the same manner of comparative example 1 except that 185 g of glycerin (0.19% Conc.), 37 g of glacial acetic acid (0.04% Conc.) and 314.5 g of sucrose fatty acid ester (0.33% Conc.) are added to the mixed solution.

Even though the improved gellation property shows compared to the capsule prepared in comparative example 1, we can not obtain the desirable hard capsule having appropriate thickness and weight can be obtained after forming a capsule using molding pin.

EXAMPLE 1

Preparation of Cellulose Capsule 18.5 kg of HPMC (19.24% Conc.) is added to 68.3 L of purified water (80~85° C.) without making an agglomerate. Then, the mixture is stirred and dispersed at 300 rpm for 120 minutes. After dispersion, the dispersed aqueous solution is stirred and solubilized until 45~50° C. Then, the mixture is cooled in room temperature by standing naturally for 24~36 hours. The solution becomes dark brown when finishing solubilization.

The mixed solution of pectin and glycerin is prepared by following steps of: i) 703 g of pectin (0.73% Conc.) is added to 6.3 L of purified water at 60° C. by stirring from 8,000 rpm to 9,700 rpm, ii) 185 g of glycerin (0.19% Conc.) is added to said mixture after solubilization of pectin, and iii) stirring the mixture continuously to make a mixed solution.

37 g of calcium gluconate (0.04% Conc.) is added to 1.8 L of purified water at 60° C. by stirring at 3,000 rpm for about 3 minutes. Table 1 shows the composition of mixed aqueous solution.

TABLE 1

Composition of mixed aqueous solution

| Component | Amount Input | Ratio Concentration |
|---|---|---|
| Purified Water | 76.4 L | 79.43% |
| Hydroxyl Propyl Methyl Cellulose | 18.5 kg | 19.24% |
| LM Amide Pectin | 703.0 g | 0.73% |
| Glycerin | 185.0 g | 0.19% |
| Glacial Acetic Acid | 37.0 g | 0.04% |
| Calcium Gluconate | 37.0 g | 0.04% |
| Sucrose Fatty Acid Esters | 314.5 g | 0.33% |

Followings are preparation steps for making a cellulose capsule.

i) Stirring for 5 minutes after solubilizing HPMC
ii) Stirring for 5 minutes after adding the mixed solution of pectin and glycerin;
iii) Stirring for 2 minutes after adding the glacial acetic acid;
iv) Stirring for 2 minutes after adding the calcium gluconate;
v) Stirring for 10 minutes after adding sucrose fatty acid ester; and
vi) Standing the solution prepared in above step.

Such prepared solution is packed in the bottle, and is heated up to 53~55° C. by standing for 12 hours. Then, the viscosity is adjusted and the bubble is completely removed for forming a capsule. The desirable hard capsule having appropriate thickness and weight can be obtained after forming a capsule using molding pin.

Pectin is not hydrolyzed during 48 hours continuous manufacturing test. Therefore, there is no problem by losing the mixture from the molding pin. The quality of cellulose hard capsule prepared in this invention can be maintained during the long drying without any change of film.

FIG. 1 shows the curve of the viscosity of the mixed aqueous solution according to the flow of time.

The temperature of time interval T1 for dispersion is at 80~85° C.; T2 for solubilization is at 45~50° C.; T3 for stabilization is at 53~55° C.; and T4 for precipitating and forming a capsule is at 53~55° C.

EXAMPLE 2

Comparison Between Cellulose Capsule and Gelatin Capsule

The properties between cellulose capsule of the present invention and commercially marketed gelatin capsule have been measured in each aspect.

Table 2 shows the comparison of film distribution.

TABLE 2

Comparison of film distribution

| Film distribution Size: #0 (n = 30) | | Invention product | Control |
|---|---|---|---|
| CE | Cap | X : 0.103<br>max : 0.114<br>min : 0.091 | X : 0.102<br>max : 0.111<br>min : 0.090 |
|  | Body | X : 0.102<br>max : 0.110<br>min : 0.093 | X : 0.101<br>max : 0.109<br>min : 0.095 |
| Top | Cap | X : 0.130<br>max : 0.160<br>min : 0.110 | X : 0.121<br>max : 0.140<br>min : 0.102 |
|  | Body | X : 0.129<br>max : 0.150<br>min : 0.101 | X : 0.125<br>max : 0.135<br>min : 0.102 |

Remark
CE means side of capsule film, Top means front of capsule.
Cap means upper capsule of the blank capsule, and Body means lower capsule of the blank capsule.

As shown in Table 2, there is no problem of film distribution caused by the decline of gellation property. However, there is some increase of thickness of Top, which seems to be caused by the property of aqueous solution.

Table 3 shows the comparison of length, weight and diameter.

TABLE 3

Comparison of length, weight and diameter

| | Invention product (#0) | Control (#0) | Remark |
|---|---|---|---|
| Length (mm) n = 30 | | | |
| Cap | X : 11.2<br>max : 11.4<br>min : 10.9 | X : 11.1<br>max : 11.5<br>min : 10.9 | Measuring Machine : Vernier Caliper Measuring Sensitivity : 0.01 mm |
| Body | X : 18.7<br>max : 18.9<br>min : 18.5 | X : 18.6<br>max : 18.8<br>min : 18.4 |  |
| Weight (mg) n = 210 | X : 98.0<br>max : 102.1<br>min : 93.0 | X : 97.5<br>max : 101.2<br>min : 93.5 | Measuring Machine : AND Balance Measuring Sensitivity 0.0001 g |
| Diameter (mm) n = 30 | | | |
| Cap | X : 7.61<br>max : 7.63<br>min : 7.60 | X : 7.63<br>max : 7.65<br>min : 7.62 | Measuring Machine : Profile project Sensitivity : 20 fold |
| Body | X : 7.33<br>max : 7.35<br>min : 7.31 | X : 7.32<br>max : 7.34<br>min : 7.30 |  |

As shown in Table 3, the cellulose capsule of the present invention shows equivalent physical property compared to marketed control product.

Table 4 shows the comparison of mobility.

TABLE 4

Comparison of mobility

| | Invention product | Control |
|---|---|---|
| Sliding test Measuring method | 23 cm<br>The measuring machine is designed by inventors. In the cylinder type of drum, 50,000 capsules are inserted for testing material. Then, the bottom of drum is open and capsules are got out from the bottom of drum. The height of the capsule remained is measured. The lower height means better mobility of the sample. | 28 cm |

As shown in Table 4, the mobility of cellulose capsule of the present invention is better than marketed control product.

Table 5 shows the comparison of filling up property.

TABLE 5

Comparison of filling up property

| | Zanasi AZ-20 | | Zanasi AZ-40 | |
|---|---|---|---|---|
| Rate | 15,600 EA/hour | | 32,000 EA/hour | |
| Pressure | 20 cmHg | | 25 cmHg | |
| Amount | each 50,000 EA | | each 100,000 EA | |
| Result | Invention product | Control | Invention product | Control |
| Water content | 5.5% | 14.0% | 5.0% | 13.5% |
| Breakage | none | none | none | none |

As shown in Table 5, the filling up property of cellulose capsule of the present invention is excellent, and there is no problem for filling up, for example, telescope or bad joint, and there is no breakage at 5% of water content.

Table 6 shows the comparison of solubility and disintegration.

TABLE 6

Comparison of solubility and disintegration

|  | Invention product | Control | Remark |
|---|---|---|---|
| Solubility (pH 6.0 ~ 7.0) | Avg. 5' 50"<br>Max. 6' 10"<br>Min. 5' 30" | Avg. 2' 50"<br>Max. 3' 01"<br>Min. 2' 30" | * Measuring method : JP 50 ml of purified water is inserted to 100 ml of flask. At 37 ±0.5° C., we measure the time required complete solubility of blank capsule of separated Cap and Body. Measured 5 times.<br>* Required standard : within 10 minutes |
| Disintegration (pH 6.0 ~ 7.0) | Avg. 14' 00"<br>Max. 14' 50"<br>Min. 13' 35" | Avg. 13' 20"<br>Max. 13' 50"<br>Min. 13' 00" | * Measuring method : JP Measuring the time required complete disintegration of blank capsule at 37 ± 0.5° C. Measured 5 times.<br>* Required standard : within 20 minutes |

As shown in Table 6, the solubility and disintegration property of cellulose capsule of the present invention is enough, even though the solubility of present invention product is slightly required more time, because the results meet with standard requirements.

Table 7 shows the comparison of transparency of film.

TABLE 7

Comparison of transparency of film

|  | Invention product | Control | Remark |
|---|---|---|---|
| Transparency of film (%) | 50% | 68% | * Measuring Machine : UV-visible Spectroscopy HP-8453 (Made in USA, Hewlett Packard)<br>* Measuring 4 times at 570 nm UV |

As shown in Table 7, the transparency of cellulose film is enough to be used for hard capsule.

As described above, the cellulose capsule of the present invention provides an efficient cellulose capsule using pectin and glycerin, which shows good solubility, disintegration and tranparency property. The mixture of pectin and glycerin can be used as an excellent gelling agent of cellulose capsule, by replacing carrageenan or gellan gum, which enables the application of mixture of pectin and glycerin to cellulose capsule.

What is claimed is:

1. A process for preparing a cellulose capsule, which process comprises the following steps:
    i) preparing a mixed solution of pectin and glycerin;
    ii) adding the mixed solution to an aqueous solution of solubilized cellulose;
    iii) adding glacial acetic acid, calcium gluconate and sucrose fatty acid ester to the resulting admixture; and
    iv) allowing the thus-obtained product to stand, adjusting its viscosity, and forming a capsule from it.

2. The process for preparing a cellulose capsule according to claim 1, wherein the cellulose capsule comprises from 15~23 wt % of cellulose derivatives, from 0.3~1.1 wt % of amide pectin, and from 0.04~0.6 wt % of glycerin.

3. The process for preparing a cellulose capsule according to claim 2, wherein raw materials of the cellulose capsule comprise from 18~20 wt % of solubilized cellulose in aqueous solution, from 0.6~0.8 wt % of low methoxyl amide pectin, from 0.1~0.3 wt % of glycerin, from 0.03~0.05 wt % of glacial acetic acid, from 0.03~0.05 wt % of calcium gluconate, and from 0.2~0.5 wt % of sucrose fatty acid ester.

4. The process for preparing a cellulose capsule according to claim 1, wherein the pectin is low methoxyl amide pectin.

5. A cellulose capsule prepared by a process as claimed in claim 1.

6. A composition comprising an admixture of glacial acetic acid, calcium gluconate and sucrose fatty acid in combination with a product, wherein the product is that of a pectin and glycerin solution in combination with an aqueous solution of solubilized cellulose.

7. A cellulose capsule having a composition which is that of claim 6.

8. The cellulose capsule according to claim 7, wherein the pectin is low methoxyl amide pectin.

9. The cellulose capsule according to claim 8, the composition of which is a product of from 18~20 wt % of cellulose derivative, from 0.6~0.8 wt % of low methoxyl amide pectin, from 0.1~0.3 wt % of glycerin, from 0.03~0.05 wt % of glacial acetic acid, from 0.03~0.05 wt % of calcium gluconate, and from 0.2~0.5 wt % of sucrose fatty acid ester.

10. A cellulose capsule which has a composition that is a product of a pectin and glycerin solution in combination with an aqueous solution of solubilized HPMC, the product being in admixture with glacial acetic acid, calcium gluconate and sucrose fatty acid.

11. A process as claimed in claim 1 wherein step (i) comprises preparing a mixed solution of from 0.3 to 1.1 wt. % of pectin and from 0.4 to 0.6 wt. % of glycerine; step (ii) comprises adding the mixed solution to an aqueous solution of from 15 to 23 wt. % of solubilized cellulose; and step (iii) comprises adding from 0.03 to 0.05 wt. % of glacial acetic acid, from 0.03 to 0.5 wt. % of calcium gluconate and from 0.2 to 0.5 wt. % glucose fatty acid ester to the resulting admixture.

12. A process according to claim 1 wherein the solubilized cellulose is hydroxy-propylmethyl cellulose.

* * * * *